(12) United States Patent
Marion et al.

(10) Patent No.: US 8,373,002 B2
(45) Date of Patent: Feb. 12, 2013

(54) PRODUCTION OF NITRILE COMPOUNDS

(75) Inventors: Philippe Marion, Vernaison (FR); Amélie Hynaux, Plaisir (FR); Dorothée Laurenti, Rillieux-la pape (FR); Christophe Geantet, Miribel (FR)

(73) Assignees: Rhodia Operations, Aubervilliers (FR); Centre National de la Recherche Scientifique, Paris (FR)

( * ) Notice: Subject to any disclaimer, the term of this patent is extended or adjusted under 35 U.S.C. 154(b) by 243 days.

(21) Appl. No.: 12/812,891

(22) PCT Filed: Jan. 12, 2009

(86) PCT No.: PCT/EP2009/050253
§ 371 (c)(1), (2), (4) Date: Dec. 22, 2010

(87) PCT Pub. No.: WO2009/092637
PCT Pub. Date: Jul. 30, 2009

(65) Prior Publication Data
US 2011/0082310 A1    Apr. 7, 2011

(30) Foreign Application Priority Data

Jan. 18, 2008   (FR) ..................................... 08 00255

(51) Int. Cl.
| | | |
|---|---|---|
| *C07C 253/10* | (2006.01) | |
| *C07C 253/24* | (2006.01) | |
| *C07C 253/34* | (2006.01) | |
| *C07C 1/32* | (2006.01) | |

(52) U.S. Cl. ......... 558/335; 558/336; 585/733; 423/358
(58) Field of Classification Search .................. None
See application file for complete search history.

(56) References Cited

U.S. PATENT DOCUMENTS

| 2,105,831 | A | * | 1/1938 | Andrussow ................... 423/376 |
|---|---|---|---|---|
| 2,590,146 | A | * | 3/1952 | Barsky .......................... 423/352 |
| 2,706,675 | A | * | 4/1955 | Chatelain ..................... 423/372 |
| 3,752,839 | A | * | 8/1973 | Drinkard, Jr. et al. ........ 558/340 |
| 4,389,348 | A | * | 6/1983 | Diamond et al. ............. 558/459 |
| 6,162,351 | A | * | 12/2000 | Sudhakar et al. ....... 208/216 PP |
| 6,221,327 | B1 | * | 4/2001 | DeCourcy et al. ............ 423/376 |
| 7,084,293 | B2 | * | 8/2006 | Rosier et al. .................. 558/335 |
| 7,294,325 | B2 | * | 11/2007 | Ehrhardt et al. .............. 423/372 |
| 7,485,741 | B2 | | 2/2009 | Bourgeois et al. |
| 7,501,045 | B2 | | 3/2009 | Gerber et al. |
| 7,537,744 | B2 | * | 5/2009 | Benderly et al. ............. 423/238 |
| 7,897,801 | B2 | * | 3/2011 | Rosier et al. .................. 558/334 |
| 8,039,660 | B2 | * | 10/2011 | Basset et al. ................. 558/338 |
| 2011/0112202 | A1 | * | 5/2011 | Marion et al. ................ 518/702 |

FOREIGN PATENT DOCUMENTS

| FR | 2847898 | 6/2004 |
|---|---|---|
| FR | 2857965 | 1/2005 |

OTHER PUBLICATIONS

Baker, Michael J. et al., "Chelating Diphosphite Complexes of Nickel(0) and Platinum(0): Their Remarkable Stability and Hydrocyanation Activity", J. Chem. Soc., Chem. Commun., 12, 803-804, 1991.*

Hollod, G. J. et al., "Hazardous Waste Minimization: Part I. Waste Reduction in the Chemical Industry Du Pont's Approach", JAPCA, 38(2), 174-179, 1988.*

Manzer, Leo E., "Chemistry and Catalysis. Keys to Environmentally Safer Processes", ACS Symposium Series, 577 (Benign by Design), 144-154, 1994.*

* cited by examiner

*Primary Examiner* — Fiona T Powers
(74) *Attorney, Agent, or Firm* — SNR Denton US LLP

(57) ABSTRACT

Organic compounds containing at least one site of ethylenic unsaturation are catalytically hydrocyanated and the medium of hydrocyanation is separated into desired linear organic compounds containing at least one nitrile function, e.g., 3-pentenenitrile, and undesired nitrile by-products, e.g., methylglutaronitrile, and the undesired nitrile by-products are hydrodenitrogenated into ammonia and at least one hydrocarbon compound under an absolute hydrogen pressure ranging from 0.1 to 10 MPa at a temperature ranging from 200° to 500° C. and in the presence of a hydrodenitrogenation catalyst.

11 Claims, No Drawings

US 8,373,002 B2

PRODUCTION OF NITRILE COMPOUNDS

CROSS-REFERENCE TO PRIOR APPLICATIONS

This application claims priority under 35 U.S.C. §119 of FR 0800255, filed Jan. 18, 2008, and is a continuation of PCT/EP 2009/050253, filed Jan. 12, 2009 and designating the United States (published in the French language on Jul. 30, 2009, as WO 2009/092637 A1; the title and abstract were also published in English), each hereby expressly incorporated by reference in its entirety and each assigned to the assignee hereof.

The present invention relates to a process for preparing hydrocarbon compounds containing at least one nitrile function.

It relates more particularly to a process for preparing nitrile compounds by hydrocyanation of compounds containing at least one ethylenic unsaturation. This process comprises a step of treatment of the unexploitable by-products containing at least one nitrile function to convert them to ammonia and exploitable hydrocarbon compounds.

The processes for preparing hydrocarbon compounds containing at least one nitrile function, especially a compound containing two nitrile functions, such as adiponitrile, are practised industrially on a large scale. Of these processes, the one which utilizes the two-step hydrocyanation reaction of butadiene has been exploited since the 1970s. The great majority of worldwide production of adiponitrile is obtained by this process.

Adiponitrile is a major chemical intermediate which is used in the production of hexamethylenediamine, an important monomer for the preparation of polymers, especially of polyamides, and for that of isocyanates. The process of hydrocyanating butadiene comprises, in a first step, adding a molecule of hydrocyanic acid to a double bond to produce unsaturated mononitrile compounds. The mononitrile compounds obtained are linear compounds such as 2-pentenenitrile and 3-pentenenitrile, or branched compounds, such as 2-methyl-2-butenenitrile and 2-methyl-3-butenenitrile.

In a second step, a second molecule of hydrocyanic acid is added to the unsaturation of the mononitrile compounds. Among the aforementioned mononitriles, only 3-pentenenitrile can be converted to adiponitrile; the other compounds lead to branched dinitrile compounds which cannot be exploited for the production of hexamethylenediamine.

Moreover, the addition of HCN to the unsaturation of 3-pentenenitrile permits preparation primarily of adiponitrile but also of 2-methylglutaronitrile (MGN) and 2-ethylsuccinonitrile (ESN). The quantity of MGN produced varies according to the nature of the catalyst system used. Furthermore, the mononitrile compounds other than the 3-PN that are introduced in the second step either are converted to dinitrile compounds other than adiponitrile, which cannot be exploited for the production of hexamethylenediamine, or are not hydrocyanated. Thus the compound 2-pentenenitrile (2-PN) is not hydrocyanated and is recovered by distillative separation in the form of a stream of unexploitable by-products.

To enhance the selectivity of the first step towards 3-pentenenitrile compound, the process for preparing adiponitrile comprises an isomerization step which makes it possible in particular to convert 2-methyl-3-butenenitrile to 3-pentenenitrile.

In the present text, exploitable compounds or products are the compounds which can be used as starting materials in chemical reactions for synthesizing important chemical compounds such as adiponitrile, diamines (hexamethylenediamine) and aminonitriles (aminocapronitrile). By unexploitable by-products are meant the products formed during the hydrocyanation process that cannot be used economically as a starting material for the preparation of new products and which are considered in the process of hydrocyanation to be effluents, to be treated before being expelled into the environment.

These unexploitable by-products are most commonly destroyed by incineration in boilers for producing steam. Some of them, however, may be wholly or partially exploited by chemical conversion to new, useful compounds. Thus the most important by-product in terms of quantity is 2-methylglutaronitrile (MGN), which in particular can be hydrogenated to produce a branched diamine, 2-methylpentamethylenediamine (MPMD), which is used principally as a monomer for the preparation of polyamide or as a starting material for the synthesis of chemical products. Other ways of exploiting MGN have been described.

The other dinitrile or mononitrile by-products are essentially exploited by combustion to produce energy. Since, however, these compounds contain nitrogen atoms, the combustion gases produced contain nitrogen atoms. It may therefore be necessary to treat these combustion gases in units for converting and destroying oxides of nitrogen, referred to as DENOx units.

The problem of treating and exploiting unexploitable by-products in, in particular, the process of hydrocyanating butadiene has therefore still not been fully solved, and new solutions are constantly sought.

One of the aims of the present invention is to provide a process for treating these by-products that does not exhibit the drawbacks of combustion and that allows the overall economics of the process to be enhanced, in particular by exploiting the by-products in the form of compounds which are exploitable in and advantageously recyclable to the process for preparing adiponitrile.

The invention accordingly provides a process for producing linear organic compounds containing at least one nitrile function by hydrocyanation of an organic compound containing at least one ethylenic unsaturation in the presence of a catalyst system, comprising one or more steps of separating the exploitable nitrile compounds and unexploitable nitrile by-products from the hydrocyanation medium or media, characterized in that it comprises treating the unexploitable by-products in a hydrodenitrogenation or hydrotreating step by reaction with hydrogen under an absolute pressure of between 0.1 and 10 MPa, preferably from 0.5 MPa to 3 MPa, at a temperature of between 200° C. and 500° C., preferably from 300° C. to 400° C., in the presence of a hydrodenitrogenation catalyst in order to convert said by-products to ammonia and hydrocarbon compounds.

The process of the invention allows some or all of the streams of unexploitable by-products containing nitrile functions that are generated in the processes of hydrocyanating olefins, more particularly butadiene, to be treated for the purpose of recovering the nitrogen atom in ammonia form and the major part of the carbon and hydrogen atoms in the form of hydrocarbon compounds containing one or more carbon atoms.

This hydrotreating may also be accompanied by thermal cracking of the hydrocarbon chains, leading to the formation of hydrocarbon compounds without a nitrogen atom and/or of hydrocarbon compounds containing nitrogen atoms. The latter may be converted to hydrocarbon compounds by reaction with hydrogen, according to the operating conditions employed. Furthermore, cyclic compounds containing nitrogen atoms may also be formed, such as picolines. According to the invention, the term % HDN or yield of the treatment process of the invention is applied to the ratio, expressed as a percentage, of the number of moles of hydrocarbon compounds containing no nitrogen atom that are produced either by hydrotreating or by thermal cracking, relative to the number of moles of compounds to be treated that are employed.

Following separation and recovery of the ammonia, these hydrocarbon compounds may be exploited as they are or fed to a steam reforming and methanation step to be converted to methane, a product which can be exploited in particular as an energy generator and starting material for the synthesis of numerous compounds, such as hydrocyanic acid, and hydrogen.

Thus, in the process for hydrocyanating butadiene, hydrocyanic acid (HCN), one of the main reactants of the process, is generated upstream of the hydrocyanation step. This production of hydrocyanic acid is generally carried out by using the Andrussow process, which comprises reacting natural gas, whose main constituent is methane, with ammonia in the presence of oxygen or an oxygen-containing gas.

The process of the invention, which produces ammonia and methane by hydrodenitrogenation of the unexploitable by-products and steam reforming/methanation of the hydrocarbon compounds obtained, allows the recycling, advantageously, of the ammonia and methane thus produced to the hydrocyanic acid synthesis step. Consequently the amounts of ammonia and of natural gas or methane that are consumed per tonne of adiponitrile produced are significantly reduced.

According to another characteristic of the invention, the hydrodenitrogenation catalyst comprises a metallic element belonging to the group of noble metals consisting of platinum, palladium, rhodium and ruthenium, or a transition metal such as nickel. Preference is given to using platinum.

Advantageously and preferably, the catalyst is of the supported catalyst type, in which the metallic catalytic element is supported on a material, preferably a porous material, such as alumina, silica, aluminosilicates, silica-aluminas, activated carbons, zirconia, titanium oxide and zeolites.

The preferred catalyst of the invention comprises platinum deposited on a support selected from the group consisting of silica, alumina, zirconia, silica-aluminas and zeolites.

The hydrodenitrogenation or hydrotreating reaction is carried out in the presence of a heterogeneous catalyst which either is dispersed in suspension in the reactor or is in the form of a fixed bed or fluidized bed through which the stream of nitrile compounds is fed. The catalyst may also be deposited on a monolithic support in honeycomb form.

The present invention is not limited to these embodiments, which are given solely as an illustration.

The preferred hydrodenitrogenation catalysts of the invention are, in particular, platinum-on-zirconium and platinum-on-silica-alumina catalysts.

The degree of conversion (% HDN) of the nitrile compounds employed is very high, close to or equal to 100%. The products recovered are ammonia and, in the majority, hydrocarbon compounds. Thus the treatment of 2-methylglutaronitrile produces, as hydrocarbon compounds, 2-methylpentane in very much a majority.

The mixture of compounds recovered is advantageously treated to separate and recover the ammonia, by distillation, for example.

According to one preferred characteristic of the invention the hydrocarbon compounds, especially 2-methylpentane, may be a chain-linking process comprising a steam reforming followed by a methanation to produce methane. This steam reforming/methanation treatment is very widely used in the petroleum industry, and can be implemented by heating in the presence of a catalyst (catalytic steam reforming). Typical catalysts for these reactions include supported nickels. This process is carried out at a temperature of between 200 and 700° C. under a pressure of between 5 and 50 bar.

It may also be of advantage to submit the hydrocarbon compounds obtained in the hydrodenitrogenation step solely to a steam reforming treatment. The hydrogen and carbon monoxide that are recovered can be directly exploited together or separately.

When the hydrocarbon compounds formed in the hydrodenitrogenation step have to be subjected to steam reforming, it is preferable to remove the traces of ammonia present in these hydrocarbon compounds, so as not to impair the performance efficiencies of the steam reforming and of the methanation.

A general description of the processes of thermal or catalytic steam reforming and methanation is given in the work "Les procédés de pétrochemie", TECHNIP, volume 1, 1965, whose authors are A. Chauvel, G. Lefebvre and L. Castex.

The process of the invention is applied in particular to the process for preparing adiponitrile by hydrocyanation of butadiene in two steps. This process is described in numerous patents, and a detailed description is available in RAPPORTS SRI No. 31, Supplement B, entitled "Hexamethylene Diamine".

Briefly stated, in a process for hydrocyanating butadiene, the first step comprises attaching a molecule of HCN to a double bond of the butadiene. This step is carried out in the presence of a catalytic system comprising a metallic element, preferably nickel, complexed with organophosphorus ligands containing one or more phosphorus atoms. These organophosphorus ligands are selected from organophosphites, organophosphonites, organophosphinites and organophosphines. Of these ligands, tritolyl phosphite has been used industrially since the 1970s.

Other compounds containing two phosphorus atoms and referred to as bidentate ligands have also been proposed in numerous patents. Likewise proposed has been the use of a catalytic system comprising a mixture of monodentate organophosphite ligands and a bidentate ligand, permitting the use of a reduced amount of bidentate ligand relative to the nickel.

The mononitrile compounds formed in this step are numerous. The compounds formed include the linear mononitriles 2-pentenenitrile (2PN) and 3-pentenenitrile (3PN), and the branched mononitriles such as 2-methyl-2-butenenitrile (2M2BN) and 2-methyl-3-butenenitrile (2M3BN).

As indicated earlier, an isomerization step is provided to convert the maximum of these branched mononitrile compounds (primarily 2M3BN) to 3-pentenenitrile compound, the only precursor of adiponitrile.

The first step generates a stream of unexploitable by-products which is not fed to the second step, and contains primarily 2M2BN.

In a second step, described earlier, the catalytic system may be equivalent or similar to that of the first step, but a cocatalyst such as a Lewis acid is added to this catalytic system. In this step, the 3-pentenenitrile is converted to adiponitrile, but also to other, branched dinitriles (methylglutaronitrile, ethylsuccinonitrile) which are separated to form a stream of effluents or of by-products which cannot be exploited to form hexamethylenediamine. In this second step, the separation of the various products contained in the reaction medium allows recovery of the 2-pentenenitrile, which was fed in at the first step and has not been converted to dinitrile compounds. This 2-pentenenitrile stream is also a stream of unexploitable by-products which will be treated according to the process of the invention.

According to the process of the invention, the streams of nitrile by-products or effluents which cannot be exploited to form 3-PN or hexamethylenediamine, which are recovered in steps 1 and 2, may be combined and treated, to be decomposed to form ammonia and alkanes, or only one of these streams may be treated. It may be advantageous to treat these streams of effluents before subjecting them to the hydrodenitrogenation step, in order, for example, to remove certain compounds, such as the phosphorus compounds, which might be poisons for the hydrodenitrogenation and/or steam reforming and/or methanation catalysts.

As indicated earlier, the ammonia and methane that are obtained by the process of the invention are advantageously recycled to the HCN synthesis plant that is generally combined with an adiponitrile production plant.

Other advantages and details of the invention will emerge more clearly from a reading of the examples, which are given below solely by way of illustration.

The tests described below were carried out with two hydrodenitrogenation catalysts:
catalyst A: Pt deposited on zirconia ($Pt/ZrO_2$)
catalyst B: platinum deposited on a silica-alumina containing a weight percentage of silica of 10, referred to as Pt/SiAl10.

Catalyst A was obtained using a zirconia support with a specific surface area of 83 $m^2/g$.

Catalyst B comprises a silica-alumina support with a specific surface area of 352 $m^2/g$, which is sold by Condea under the trade name SIRAL10. This support contains 10% by weight of $SiO_2$.

These catalysts are prepared in accordance with the procedure below:

The supports are impregnated with a solution of hexachloroplatinic acid $H_2PtCl_6$. They are left to age at ambient temperature for two hours to allow the solution to penetrate the pores. The products are then dried overnight (>12 h) at 110° C. and subsequently calcined in a stream of air at 500° C. for 1 hour (air flow rate of 60 $cm^3$ $min^{-1}$, temperature ramp of 2° C. $min^{-1}$) for decomposition of the precursor complex to form platinum oxide. They are then reduced in a stream of hydrogen at 310° C. for 6 hours (hydrogen flow rate of 60 $cm^3$ $min^{-1}$, temperature ramp of 1° C. $min^{-1}$) to give a deposit of metallic platinum.

The physicochemical characteristics of the $Pt/ZrO_2$ and Pt/SiAl10 catalysts are collated in Table 1.

The dispersion and platinum particle size were determined by hydrogen chemisorption. The platinum was assayed by plasma emission spectrometry.

TABLE 1

| Catalyst | % by mass of Pt | Dispersion [%] | $S_{particle}$ [nm] |
|---|---|---|---|
| A | 1.1 | 60 | 1.7 |
| B | 1.1 | 66 | 1.4 |

In Examples 1 to 4, the abbreviations used have the meanings indicated below:
MP: 2-methylpentane
MPip: 3-methylpiperidine
Pic: picolines (β-picoline, 2-amino-3-picoline, 6-amino-3-picoline)
% HDN: percentage of hydrocarbon products containing no nitrogen atom, relative to the number of moles of compounds to be treated that are employed.

EXAMPLE 1

Hydrodenitrogenation of MGN Under an Absolute Pressure of 0.1 MPa Using Catalyst A The hydrodenitrogenation (HDN) reaction of methylglutaronitrile was carried out at various temperatures and under an absolute pressure of 0.1 MPa with a hydrogen flow rate of 55 ml/min and a fixed bed of catalyst A with a mass of 15 mg, according to the following procedure, in a dynamic microreactor.

The reaction mixture comprises pure 2-methylglutaronitrile and hydrogen. The hydrogen, whose flow rate is regulated by a mass flow meter (0-200 ml/min), bubbles into a saturator which is filled with liquid MGN, then passes into a condenser whose temperature controls the partial pressure of MGN. The MGN partial pressure is 1.33 kPa. The reactor is placed in a tubular oven whose temperature is controlled by a platinum probe regulator. The reaction temperature is measured by means of a thermocouple sited at the catalyst bed.

To prevent the condensation of the reactant and of the reaction products, the temperature of the apparatus assembly is consistently maintained at 180° C. A trap is sited at the exit of the test to condense the reaction products and the unconverted reactant. The gases then leave at the vent. The compounds recovered are primarily 2-methylpentane (MP) as hydrocarbon compounds and 3-methylpiperidine (MPip) and picoline or its derivatives, denoted collectively by Pic, as compounds containing a nitrogen atom.

The different yields obtained are collated in Table II below:

TABLE II

| T [°] | 250 | 300 | 350 | 400 | 450 |
|---|---|---|---|---|---|
| Nitrogen-containing products (including Pic and MPip) [%] | 70.3 (3.6-61.1) | 78.6 (65-5.3) | 74 (58.6-0) | 64.9 (27.7-0) | 67 (10.9-0) |
| Hydrocarbon products (including MP) [%] | 0.3 (0.3) | 2.6 (1.7) | 3.7 (1.2) | 13 (0.7) | 12 (0.2) |

EXAMPLE 2

Hydrodenitrogenation of MGN Under an Absolute Pressure of 0.1 MPa Using Catalyst B Example 1 is repeated except for the type of catalyst, which is catalyst B.

The yields obtained are collated in Table III below:

TABLE III

| T [°] | 250 | 300 | 350 | 400 | 450 |
|---|---|---|---|---|---|
| Nitrogen-containing products (including Pic and MPip) [%] | 61.3 (4.4-50) | 68.3 (57.5-2.5) | 65.7 (48-0) | 58.7 (25.9-0) | 43.8 (9.9-0) |
| Hydrocarbon products (including MP) [%] | 0.3 (0.3) | 1.4 (1.1) | 4.8 (1.4) | 18.3 (1.2) | 40.4 (0.7) |

EXAMPLE 3

Hydrodenitrogenation of MGN Under an Absolute Pressure of 1 MPa Using Catalyst A Example 1 is repeated using 50 mg of catalyst A with an absolute pressure of 1 MPa, an MGN partial pressure of 1.33 kPa and a hydrogen flow rate of 16 ml/min. When the tests are carried out under pressure, the reaction mixture is injected, after letdown to atmospheric pressure, into a gas chromatograph via a six-way valve.

The yields obtained are collated in Table IV below:

TABLE IV

| T [°] | 250 | 300 | 350 | 400 |
|---|---|---|---|---|
| Nitrogen-containing products (including Pic and MPip) [%] | 93.9 (1.5-92.4) | 67.1 (15.4-51.7) | 46.1 (41.8-4.3) | 55.9 (55.6) |
| Hydrocarbon products (including MP) [%] | 4.1 (2.8) | 32.1 (32.1) | 49.5 (44) | 22.2 (11.4) |

EXAMPLE 4

Hydrodenitrogenation of MGN Under an Absolute Pressure of 1 MPa Using Catalyst B Example 3 is repeated except for the type of catalyst, which is catalyst B.

The yields obtained are collated in Table V below:

TABLE V

| T [°] | 250 | 300 | 350 | 400 |
|---|---|---|---|---|
| Nitrogen-containing products (including Pic and MPip) [%] | 65.6 (0.9-64.7) | 4.4 (1.3-3.1) | 0 (48) | 3.4 (3.4-0) |
| Hydrocarbon products (including MP) [%] | 34.4 (32.9) | 95.6 (90.7) | 100 (86.3) | 96.6 (54.9) |

EXAMPLE 5

Hydrodenitrogenation of MGN Under an Absolute Pressure of 0.55 MPa Using Catalyst B Example 4 is repeated under an absolute pressure of 0.55 MPa with a hydrogen flow rate of 4 ml/min and an MGN partial pressure of 1.33 kPa.

The yields obtained are collated in Table VI below:

TABLE VI

| T [°] | 250 | 300 | 350 |
|---|---|---|---|
| Nitrogen-containing products (including Pic and MPip) [%] | 30.3 (2.5-27.8) | 0 (0-0) | 0.3 (0.3-0) |
| Hydrocarbon products (including MP) [%] | 69.8 (68.6) | 100 (93.9) | 99.7 (78.5) |

These results show that the catalytic activity for hydrodenitrogenation of MGN is low under atmospheric pressure for a temperature of between 250° C.< and <350° C.

Under a pressure of 1 MPa, the yield in the hydrodenitrogenation of MGN is higher, and reaches a value of 100% for a temperature of 350° C.

Under a pressure of 0.55 MPa it is also possible to obtain a yield of 100% in the hydrodenitrogenation of MGN, for a temperature of 300° C.

EXAMPLE 6

Hydrodenitrogenation of a By-Product Obtained from a Unit for Preparing Adiponitrile by Hydrocyanation of Butadiene, Over Catalyst B Producers of adiponitrile sell a number of by-products or effluents originating from the preparation of adiponitrile by hydrocyanation of butadiene. Thus the by-product containing primarily 2-methylglutaronitrile, representing a distillation fraction recovered in the process of separating adiponitrile, is sold under the name MGN stream.

This MGN stream was used to carry out Examples and following. It has the following composition by weight:

| | |
|---|---|
| 2-methylglutaronitrile | 85% |
| ethylsuccinonitrile | 11% |
| adiponitrile | 3% |
| other compounds | 1% |

The hydrodenitrogenation (HDN) reaction of the crude MGN above was carried out at different temperatures, under an absolute pressure of 0.55 MPa (hydrogen flow rate of 4 ml/min and MGN partial pressure of 1.33 kPa) with a mass of catalyst B of 50 mg, in accordance with the procedure described in Example 5.

TABLE VII

| T [° C.] | 300 | 350 | 400 |
|---|---|---|---|
| Nitrogen-containing products in % | 4.1 | 3.5 | 9.3 |
| Hydrocarbon products in % | 92.1 | 93.3 | 88.3 |

EXAMPLE 7

Hydrodenitrogenation of a By-Product Obtained from a Unit for Preparing Adiponitrile by Hydrocyanation of Butadiene Example 6 was repeated under an absolute pressure of 1 MPa for a hydrogen flow rate of 16 ml/min and an MGN partial pressure of 1.33 kPa. Under these conditions at 300° C., the % HDN is 100%.

EXAMPLE 8

Example 6 was repeated under an absolute pressure of 0.55 MPa but using, as the catalyst, a commercial platinum catalyst supported on zeolite, sold by Sud Chemie. This catalyst contains 0.3% by weight of Pt and has an Si/Al atomic ratio of 11.5.

The results are collated in Table VIII below:

TABLE VIII

| T [° C.] | 250 | 300 | 350 |
|---|---|---|---|
| Nitrogen-containing products in % | 80.1 | 70.2 | 72.9 |
| Hydrocarbon products in % | 2.9 | 22.1 | 26.1 |

EXAMPLE 9

Example 6 was repeated under an absolute pressure of 0.55 MPa but using, as the catalyst, a commercial platinum catalyst supported on zirconia, sold by Johnson Matthey. This catalyst contains 1% by weight of Pt.

The results are collated in Table IX below:

TABLE IX

| T [° C.] | 250 | 300 | 350 |
|---|---|---|---|
| Nitrogen-containing products in % | 65.4 | 2.6 | 4.7 |
| Hydrocarbon products in % | 28.5 | 97.5 | 95.3 |

EXAMPLE 10

Steam Reforming and Methanation of Methylpentane

A stream of 5 g/h of methylpentane is fed to a reactor in gas phase in parallel with a water stream of 7.5 g/h.

The reactor contains approximately 100 ml of a nickel-based catalyst supported on alumina (70% by weight of nickel). The temperature is maintained at about 550° C. by external heating. The pressure is regulated at 23 bar. On exiting, the gas is cooled and fed directly to a second reactor, containing 100 ml of Ni catalyst supported on alumina, operating under 16 bar and at 270° C. This second reactor is also fed with a constant flow rate fixed at 15 Nl/h of hydrogen. On exiting, the gases are analysed by gas chromatography.

The conversion of the methylpentane is greater than 98%. Methane is the only hydrocarbon product detected.

The invention claimed is:

1. A process which comprises catalytically hydrocyanating an organic compound containing at least one site of ethylenic unsaturation and separating the medium of hydrocyanation into desired linear organic compounds containing at least one nitrile functional group and undesired nitrile by-products, and further comprising hydrodenitrogenating said undesired nitrile by-products into ammonia and at least one hydrocarbon compound under an absolute hydrogen pressure ranging from 0.1 to 10 MPa at a temperature ranging from 200° C. to 500° C. and in the presence of a hydrodenitrogenation catalyst.

2. The process as defined by claim 1, wherein the hydrodenitrogenation catalyst comprises a metallic element selected from the group consisting of platinum, palladium, rhodium, ruthenium and nickel.

3. The process as defined by claim 2, wherein the hydrodenitrogenation catalyst comprises a metallic element supported on a support selected from the group consisting of alumina, silica, aluminosilicates, silica-aluminas, activated carbons, zirconia, titanium oxide and zeolites.

4. The process as defined by claim 3, wherein the hydrodenitrogenation catalyst comprises platinum deposited on a support selected from the group consisting of zirconia, silica, alumina, aluminosilicates and silica aluminas.

5. The process as defined by claim 1, wherein the hydrogen absolute pressure ranges from 0.5 MPa to 3 MPa.

6. The process as defined by claim 1, wherein the temperature ranges from 300° C. to 400° C.

7. The process as defined by claim 1, comprising producing adiponitrile by hydrocyanation of butadiene and wherein the desired nitrile compounds comprise adiponitrile, 3-pentenenitrile, 4-pentenenitrile, 2-methyl-3-butenenitrile or mixtures thereof.

8. The process as defined by claim 7, wherein the undesired nitrile by-products comprise methylglutaronitrile, ethylsuccinonitrile, 2-pentenenitrile, 2-methyl-2-butenenitrile or mixtures thereof.

9. The process as defined by claim 1, wherein the hydrocarbon compounds recovered at the end of the hydrodenitrogenation step are treated by steam reforming and methanation to produce at least one lower alkane, after removal of ammonia.

10. The process as defined by claim 9, wherein the steam reforming and methanation is carried out in the presence of a supported nickel-based catalyst at a temperature ranging from 200 to 700° C. and under a pressure ranging from 5 to 50 bar.

11. The process as defined by claim 9, comprising producing hydrocyanic acid by reaction of ammonia with methane and wherein the ammonia formed in the hydrodenitrogenation step and/or the lower alkane formed in the steam reforming/methanation step are introduced to the step of producing hydrocyanic acid.

* * * * *